United States Patent [19]

Hafelfinger et al.

[11] Patent Number: 5,003,975
[45] Date of Patent: Apr. 2, 1991

[54] AUTOMATIC ELECTRODE CONFIGURATION OF AN IMPLANTABLE PACEMAKER

[75] Inventors: Werner Hafelfinger, Valencia; Jason A. Sholder, Northridge; Murray P. King, Simi Valley, all of Calif.; James L. Duncan, Alpharetta, Ga.

[73] Assignee: Siemens-Pacesetter, Inc., Sylmar, Calif.

[21] Appl. No.: 422,933

[22] Filed: Oct. 17, 1989

Related U.S. Application Data

[63] Continuation-in-part of Ser. No. 183,197, Apr. 29, 1988.

[51] Int. Cl.[5] ............................................. A61N 1/00
[52] U.S. Cl. ...................... 128/419 PG; 128/419 PT
[58] Field of Search ................ 128/419 PG, 419 PT, 128/421

[56] References Cited

U.S. PATENT DOCUMENTS

| | | | |
|---|---|---|---|
| 4,532,931 | 8/1985 | Mills | 128/419 PG |
| 4,549,548 | 10/1985 | Wittkampf et al. | 128/419 PG |
| 4,558,702 | 12/1985 | Barreras et al. | 128/419 PG |
| 4,628,934 | 12/1986 | Pohndorf et al. | 128/419 PG |
| 4,658,831 | 4/1987 | Reinhard et al. | 128/419 PT |
| 4,741,342 | 5/1988 | Stotts | 128/419 PG |
| 4,805,621 | 2/1989 | Heinze et al. | 128/419 PG |
| 4,917,093 | 4/1990 | Dufresne et al. | 128/421 |

Primary Examiner—George Manuel
Attorney, Agent, or Firm—Lisa P. Weinberg; Leslie S. Miller

[57] ABSTRACT

An implantable pacemaker having a unipolar/bipolar lead interchangeability includes lead impedance measuring capability for automatically measuring lead impedance, initiated by the occurrence of predetermined events, such as whenever a programming change is made, whenever capture fails to occur in response to an applied stimulation pulse, whenever the leads are changed, and whenever a significant change of lead impedance is otherwise detected. If a proper impedance measurement is not sensed for a programmed configuration, additional impedance measurements for other possible configurations are made in an ordered sequence in order to determine if an improper lead has been implanted or if a electrode has broken. If an operable configuration is found, signified by a measurement of impedance as expected, the pacemaker continues operation in that configuration, thereby assuring that capture can continue to occur until such time as the problem which has been detected can be corrected.

29 Claims, 3 Drawing Sheets

AUTOMATIC ELECTRODE CONFIGURATION OF AN IMPLANTABLE PACEMAKER

CROSS-REFERENCE TO RELATED PATENT APPLICATIONS

This is a continuation-in-part of a prior application, Ser. No. 07/183,197, filed 4/19/88, which was related to concurrently-filed copending patent application, U.S. Ser. No. 07/183,191, entitled "Lead Impedance Scanning System for Pacemakers", which application is hereby incorporated herein by reference.

BACKGROUND OF THE INVENTION

This invention relates to implantable cardiac pacemakers and, more particularly, to implantable cardiac pacemakers having the capability of being programmed to operate in either a unipolar or bipolar mode of operation, and including the capability of having either unipolar or bipolar leads connected thereto.

The technology of cardiac pacemakers has developed a high level of sophistication of system performance. The current generation of cardiac pacemakers incorporates microprocessors and related circuitry to sense and stimulate heart activity under a variety of physiological conditions. These pacemakers may be programmed to control the heart in correcting or compensating for various heart abnormalities which may be encountered in individual patients. A background description of modern cardiac pacemaker technology is set forth in U.S. Pat. No. 4,712,555, which patent is incorporated herein by reference. It is a primary goal of programmable, multiple-mode, demand-type, cardiac pacemakers to accommodate the changing requirements of a diseased or malfunctioning heart. For example, single chamber, fixed rate pacers have been used extensively in the past to correct bradycardia, or slow heart rates. Demand pacing is employed to avoid competing rhythms in patients who have some cardiac activity. Dual chamber pacing is used to treat complete or intermittent heart block by maintaining atrio-ventricular (AV) synchrony. Various other parameters (such as rate, pulse amplitude or width, sensitivity, refractory, etc.) may also need to be altered from time to time to custom-fit the pacemaker to each patient.

Programmability has also been incorporated into pacemakers to select the type of electrodes implanted, either unipolar or bipolar. A unipolar lead is one in which stimulation occurs between the cathode tip and the pacemaker case, or anode. A bipolar lead is one in which stimulation occurs between the cathode tip, however, the anode is a ring electrode spaced approximately one inch from the cathode tip. Physicians select one lead-type over the other for a variety of reasons. A unipolar lead may be chosen due to its advantage of being physically smaller and more flexible and, therefore, easier to implant. Unipolar leads also have the advantage of being less vector sensitive for intrinsic complexes (particularly premature ventricular and atrial contractions) due to the larger dipole. On the other hand, bipolar leads provide superior noise immunity to myopotentials and electromagnetic interference. It is also known that bipolar leads eliminate pectoral muscle stimulation, however, there has also been an occasional report of diaphragmatic stimulation. Since these leads are inaccessible after implantation (except by surgical procedure), the greatest advantage of bipolar leads is its capability of being noninvasively reprogrammed to either unipolar or bipolar operation.

While electronic circuitry can be, and is, incorporated within the pacemaker itself for exercising or testing various circuit components (such as the status of battery power sources, and the effectiveness of various amplifiers, waveform shaping stages and the like), it is often more difficult to test the integrity of the leads and implanted electrodes to which the pacemaker is coupled in order to verify that such leads and electrodes can function to allow for the desired pacing operation.

At the implanting of the pacemaker and electrode system, minor damage is sometimes incurred which may affect the system's electrical insulation. This type of damage may go undetected and be without present effect on the implanted system, but the condition may manifest itself after extended time in service. When a breakdown or significant degradation of the pacemaker lead insulation occurs, it can result in a loss of sensing of intrinsic cardiac events or a loss of capture due to a lessened amount of energy reaching the cardiac tissue. Based on the underlying rhythm of the patient, this may have serious or even disastrous results. The reduced output energy reaching the heart is due to partial energy being shunted to other areas through the insulation opening.

Other types of damage can also occur to a pacemaker lead at implantation or later. A fracture in a conductor coil can affect operation by reducing the energy output to the cardiac tissue by causing a substantial increase in the lead resistance to current flow. A partial fracture will cause a reduction in output energy, while a complete fracture will result in no energy reaching the heart due to an infinite resistance (open circuit). Another type of detectable error relates to the failure of the electrode tip to be in proper contact with the heart wall.

Particular methods and apparatus for scanning the implanted leads of a pacemaker system to determine lead impedance and to detect abnormalities which may signal degradation and impending failure of pacemaker leads are the subject of U.S. patent application, Ser. No. 07/183,191, filed concurrently herewith, entitled "Lead Impedance Scanning System for Pacemakers" of Christer Ekwall, assigned to the assignee of this application. The disclosure of that application is incorporated herein by reference.

Briefly, the Ekwall application discloses a scanning system for measuring the output energy delivered to the stimulation circuit during pacing and determining the lead impedance from that measurement. The thus-determined lead impedance is compared with a moving average of the measured parameter and any deviation from that average by more than a predetermined amount is considered an anomaly. Three such anomalies in succession result in an event being counted in a first event counter for future consideration by a doctor during a patient checkup or the like. The system also monitors sensed heart signals and counts as a notable event any deviations in slope of the heart signal by more than a predetermined amount. These latter events are counted in a second counter to provide information for future reference. Thus, the Ekwall system determines the integrity of the implanted leads and electrodes by making measurements during both the pacing and sensing time intervals of the pacemaker timing cycle.

U.S. Pat. No. 4,140,131 (Dutcher et al.) discloses arrangements for detecting impedance level (either too high in the case of an open circuit, or too low in the case of a short circuit) and voltage level of the power source so that a warning may be given the patient. Basically, the lead resistance is considered as part of a voltage divider circuit and lead resistance is calculated from knowledge of impressed voltage and voltage across a known series resistor. The disclosed method is but one example of ways of measuring lead impedance which might be employed in connection with the present invention. The disclosure of U.S. Pat. No. 4,140,131 is incorporated herein by reference.

U.S. Pat. No. 4,549,548 (Wittkampf et al.) discloses a programmable pacemaker system in which the selection of lead electrodes to which pacemaker output may be connected is changed during each pacer cycle to optimize the choice of unipolar and bipolar operation for given pacemaker events. According to the patent, the selection of unipolar or bipolar mode of operation is based on a determination for monitoring the amplitude of sensed heartbeat signals to determine whether the sensing operation would be performed better in the unipolar or the bipolar mode. This is directed to a determination of heart performance vis-a-vis the leads involved so as to control the selection of unipolar or bipolar sensing.

As indicated by U.S. Pat. No. 4,606,349 (Livingston et al.), it is known in the pacemaker art to provide a pacemaker that can be programmably switched to operate in either a unipolar or bipolar mode of operation. While the Livingston et al. patent suggests that a bipolar lead always be connected to the pacemaker, which lead is then used in either a bipolar (tip-to-ring) or unipolar (tip-to-case) mode of operation, there are situations where it is desirable to use a unipolar lead. A problem thus arises when such a pacemaker has a unipolar lead connected thereto but has been programmed to operate in the bipolar mode.

Similarly, if a bipolar lead is being used in a bipolar mode of operation, and if one of the conductors breaks, the pacemaker is not able to continue operation without being reprogrammed. Unfortunately, such reprogramming can only be performed by a doctor after he has diagnosed that the conductor has broken. Then, if it is the ring conductor that has broken, the pacemaker could be reprogrammed to operate in a unipolar mode of operation using the existing implanted broken bipolar lead as a unipolar lead (tip-to-case). If it is the tip conductor that has broken, the pacemaker may, in some situations, be reprogrammed to operate in a unipolar ring-to-case mode of operation. In either event, it takes careful diagnosis and reprogramming before the pacemaker can be rendered operational. For many patients, the loss of pacemaker operation for the time period between breaking of the conductor and reprogramming of the pacemaker could present a serious health risk.

What is needed, therefore, is a pacemaker that can be programmed to operate in either a bipolar or unipolar mode of operation, that can receive either bipolar or unipolar leads, and that automatically prevents a programming configuration inconsistent with the lead used. Further, there is a need to have such a pacemaker that automatically responds to a broken conductor of a bipolar lead so as to preserve whatever pacemaker operation may be available using the remaining intact conductors of the bipolar lead. The present invention addresses these and other needs.

SUMMARY OF THE INVENTION

The present invention is intended for use with an implantable pacemaker that has electrode configuration programming capabilities, as well as, unipolar/bipolar lead interchangeability (meaning that either unipolar or bipolar operation may be programmed, and either unipolar or bipolar leads may be inserted into the pacemaker connector block).

The present invention utilizes load recognition (i.e., the load impedance presented by the lead/tissue interface during a stimulation pulse) to determine the integrity of the implanted leads and to automatically change the electrode configuration to an available and operative configuration. That is, if the measured lead impedance does not fall within a prescribed range, the pacemaker will automatically change the electrode configuration between tip-to-ring and tip-to-case. In the preferred embodiment, the pacemaker is also capable of pacing and sensing from ring-to-case. Therefore, the pacemaker will automatically change the electrode configuration between tip-to-ring, tip-to-case, and ring-to-case in a prescribed sequence. Once the new configuration is determined, the pacemaker's programmed configuration is changed to the new configuration, the physician is alerted upon the next interrogation of the change, and pacing and sensing functions continue using the new configuration.

Basically, a first feature of the invention provides a special monitoring circuit within the pacemaker that performs a lead impedance measurement whenever the operating configuration of the pacemaker is programmably changed, e.g., from bipolar to unipolar or vice versa. From this measurement, a determination is made as to whether the correct impedance is present for the existing operating configuration. If the expected impedance is not measured, then a different configuration measurement is made according to a predefined sequence until a correct impedance value is measured. The occurrence of a correct measurement is then used to set the pacemaker configuration accordingly.

To illustrate how this feature of the invention works, consider a pacemaker programmed to operate in the bipolar mode but to which a unipolar lead has been connected. Because the pacemaker is programmed to operate in the bipolar configuration, it makes its initial impedance measurement from tip to ring. However, because a unipolar lead has no ring, such a measurement would yield a very large impedance, certainly not within the expected range of 200–1500 ohms. Hence, the pacemaker next makes a tip-to-case impedance measurement. This measurement, assuming a properly placed unipolar lead is present, yields a valid impedance value. This valid measurement signals the configuration circuits of the pacemaker to switch to a unipolar mode of operation. If the tip-to-case measurement also yielded an invalid impedance measurement as might occur, for example, if a bipolar lead were in place but the tip conductor became broken, then the pacemaker, as described in the preferred embodiment, would next make a ring-to-case impedance measurement. If such measurement produced a valid impedance value, then the pacemaker configuration circuits could switch to a unipolar, ring-to-case operation.

As a safety feature, similar impedance checks or measurements would be performed automatically by the pacemaker periodically to verify the condition of the leads, or automatically whenever the pacemaker detected loss of capture (i.e., failure of the heart chamber to depolarize in response to an applied stimulation pulse). Such measurements could be performed, for example, during a refractory period of the pacemaker. If the loss of capture were caused by a broken conductor within the pacemaker lead, such measurements would quickly identify which conductor had broken, and would then allow the pacemaker to switch to whatever configuration was available to use with any remaining non-broken conductors so as to again effectuate capture (and thus allow the pacemaker to fulfill its intended function despite the broken conductor within the lead).

Thus, in the preferred embodiment, it is seen that there are three impedance measurements that can be made. These are:
1. tip-to-ring,
2. tip-to-case, and
3. ring-to-case.

In the preferred embodiment, these measurements will be made beginning with the programmed configuration. For example, if bipolar operation has been programmed, then these three measurements are made in the order listed: 1, 2, and 3. If unipolar operation has been programmed, then measurements may be made in the following order: 2, 1, and 3. If unipolar operation between the ring and case is not an available pacemaker mode, then the measurements would be made first in the programmed configuration, and then the other configuration (i.e., from unipolar to bipolar or from bipolar to unipolar). Once a correct impedance measurement is found, further impedance measurements are stopped and the configuration of the pacemaker is switched to operate in accordance with the available lead configuration detected. That is, the pacing mode of operation is switched to be the same as the lead configuration of the pacemaker that yielded a valid impedance measurement.

BRIEF DESCRIPTION OF THE DRAWINGS

The above and other objects, features and advantages of the present invention will be more apparent from the following description presented in conjunction with the accompanying drawings, wherein.

DETAILED DESCRIPTION OF THE INVENTION

The following description is of the best presently contemplated mode of carrying out the invention. This description is not to be taken in a limiting sense, but is made for the purpose of describing the general principles of the invention. The scope of the invention should be determined with reference to the appended claims.

Figure 1:
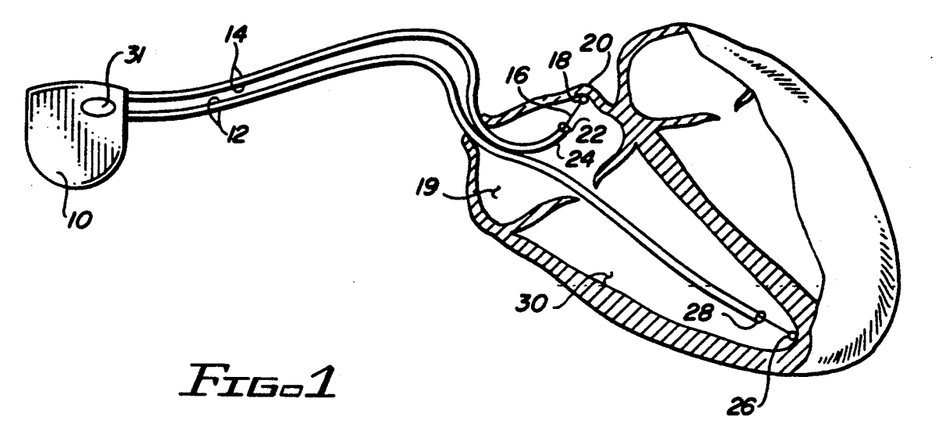
FIG. 1 is a schematic representation of a dual chamber cardiac pacemaker shown implanted in association with a heart for pacing.

Referring now to FIG. 1, there is shown a simplified representation of one way that an implanted pacemaker 10 may make electrical contact with the heart. FIG. 1 depicts the use of two bipolar leads 12 and 14, each being directed into a separate chamber of the right heart. A bipolar lead comprises a single filar that includes two electrically insulated conductors. For example, the lead 14 includes a first conductor 16 that is electrically connected to a distal tip 18 of the lead. This distal tip is typically placed in a cavity of the right atrium 19 referred to as the atrial appendage 20. A known distance from the distal tip 18 an electrode ring 22 is electrically connected to the other conductor 24 of the bipolar lead 14. Similarly, a distal tip 26 and a conductive ring 28 are associated with the bipolar lead 12 that is placed in the apex of the right ventricle 30. The manner in which the leads 12 and 14 are inserted into the heart, as well as the manner in which the pacemaker 10 is implanted in the body of a patient, are well known in the art. It will be understood that the pacemaker 10 is a programmable pacemaker with the capability of operating in any selected mode and in either a bipolar (tip-to-ring) or unipolar (tip-to-case) configuration. In the preferred embodiment, the pacemaker is also capable of operating in a unipolar configuration between the ring and the pacemaker case.

The diagram of FIG. 1 may be considered to represent a pacer operating in the VVI mode if the bipolar lead 14 with its associated distal tip 18 and electrode ring 22 is eliminated from the figure so that only the bipolar lead 12 is left with its tip and ring 26, 28 inserted in the right ventricle 30, as shown in FIG 1.

Figure 1A:
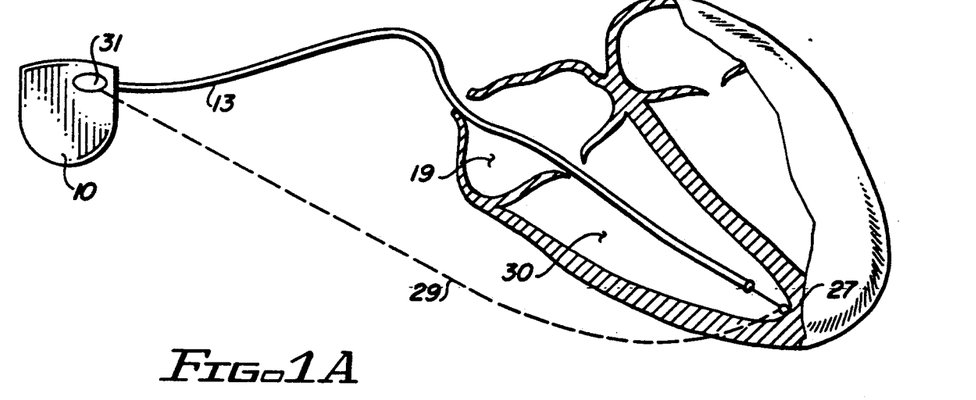
FIG. 1A is a schematic representation of a single chamber cardiac pacemaker shown implanted in association with a heart for unipolar lead pacing.

FIG. 1A is a diagram similar to that of FIG. 1 but showing the pacemaker 10 connected to a single insulated lead 13 which has a tip electrode 27 implanted in the apex of the ventricle 30 for operation as a unipolar pacemaker. Lead 13 is a single conductor, insulated lead with its sole conductor extending at an exposed metal tip 27. The return path for current between the tip electrode 27 and the case of the pacemaker 10 to an exposed region 31 is indicated by the broken line 29. A unipolar pacemaker may be used for both stimulation and sensing, although it may be somewhat more sensitive to interference from external signals such as muscle contraction or electromagnetic interference because of the dipole for sensing.

Figure 2:
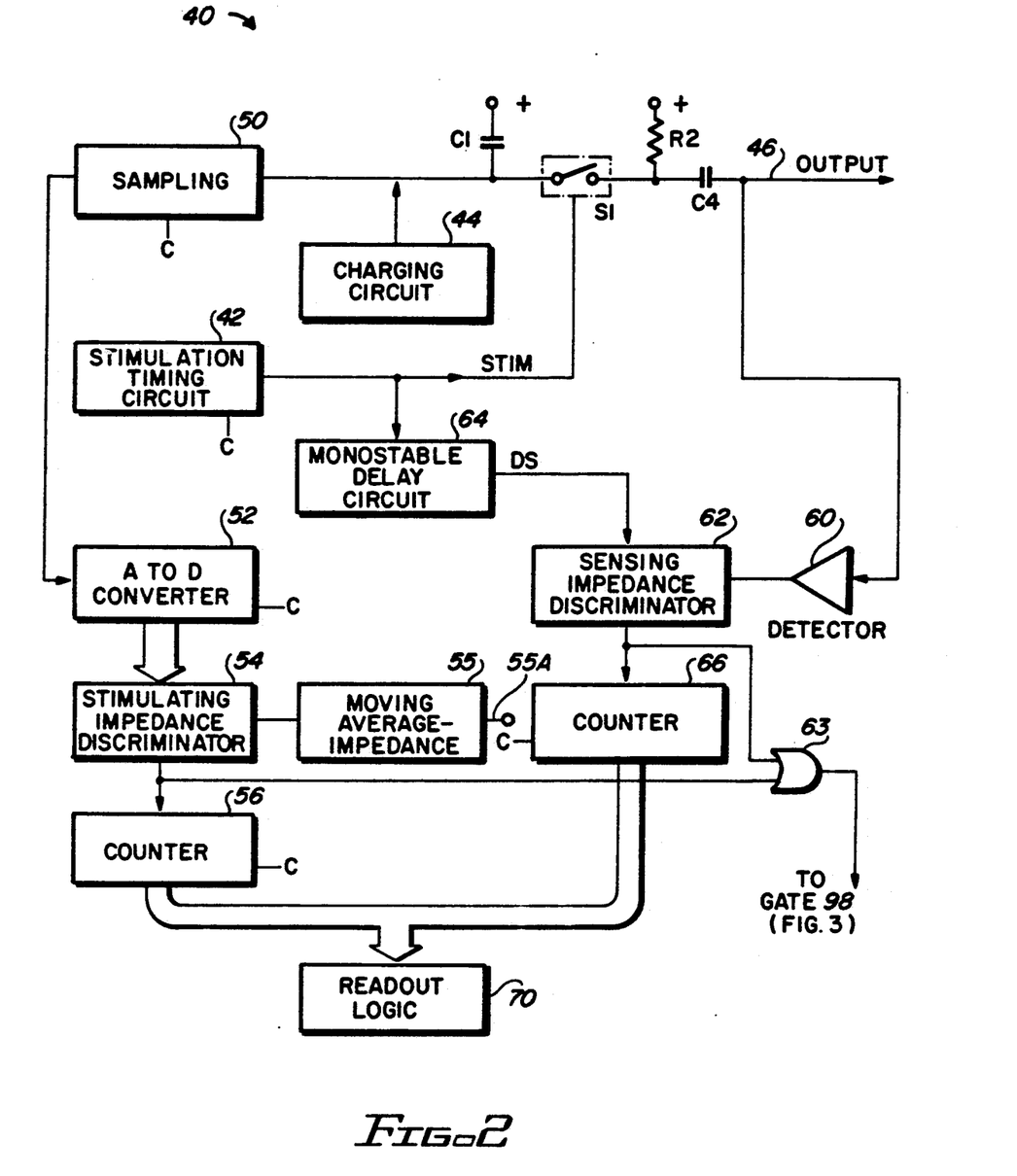
FIG. 2 is a schematic block diagram of one particular arrangement disclosed in the above-referenced Ekwall application for incorporation in a pacemaker like that shown in FIG. 1.

A block diagram of a circuit disclosed in the above-identified application of Ekwall is shown in FIG. 2. The lead impedance analyzing circuit 40 is shown comprising a stimulation timing circuit 42 which contains the normal pacemaker timing and logic circuitry. The stimulation timing circuit 42 is coupled to control the actuation of a switch S1 upon the occurrence of a stimulation signal STIM. The source of the pacing output at terminal 46 is a capacitor C1 which is coupled to be charged by a charging circuit 44 and which delivers the pacing pulse to the output 46 through a series capacitor C4 when the switch S1 is closed. Resistor R2 is provided to complete the circuit to capacitor C4 when switch S1 is open.

A sampling stage 50 is coupled to sample capacitor C1 before and after delivery of the pacing pulse. Sampled voltages from the sampling stage 50 are delivered to an analog-to-digital (A/D) converter 52, the output of which in digital form is applied to a stimulating impedance discriminator 54 which contains the circuitry for evaluating changes in lead impedance as a function of the voltage difference between the two levels sampled before and after delivery of a stimulation pulse, corresponding to the following equation:

$$R = Tp/(C1 \ln(1 - dV/Vo)) \quad (1)$$

where
R represents a lead impedance,
Tp is the stimulation pulse duration,
C1 is the source capacitor for the stimulation pulse,
Vo is the source voltage, and
dV is the voltage difference between the sampled voltages.

The stimulating impedance discriminator 54 maintains a moving average of lead impedance measurements, displayed in stage 55, according to Equation (1) and compares each new measurement with that average. If the measurement of lead impedance differs from the moving average by a predetermined value, an associated counter 56 is incremented to count the event as the occurrence of an error.

A sensing detector 60 is coupled to the terminal 46 to respond to sensed heart activity. The output of the sensing detector 60 is applied to a sensing impedance discriminator 62 which receives a delayed signal DS from a monostable delay circuit 64 that is triggered by the STIM output of the stimulation timing circuit 42. The output of the sensing impedance discriminator 62 is applied to a second counter 66. The sensing impedance discriminator 62 responds to the slope (slew) of the signal from the sensing detector 60 such that when a rate of change greater than 10 volts per second is detected, the count in the counter 66 is incremented. A readout logic stage 70 is coupled to the outputs of both counter stages 56 and 66 to provide an indication of the number of errors detected by the respective portions (stimulating signal and sensing signal) of the lead impedance analyzing circuit 40. The inputs designated by the letter C indicate connections from the various stages to a system clock (not shown). For use in the present invention, an OR gate 63 is coupled to send a signal to a gate 98 in FIG. 3 upon the occurrence of an event which would increment either counter 56 or 66, thus signaling the circuit of FIG. 3 that a significant departure from normal impedance has been detected.

Figure 3:
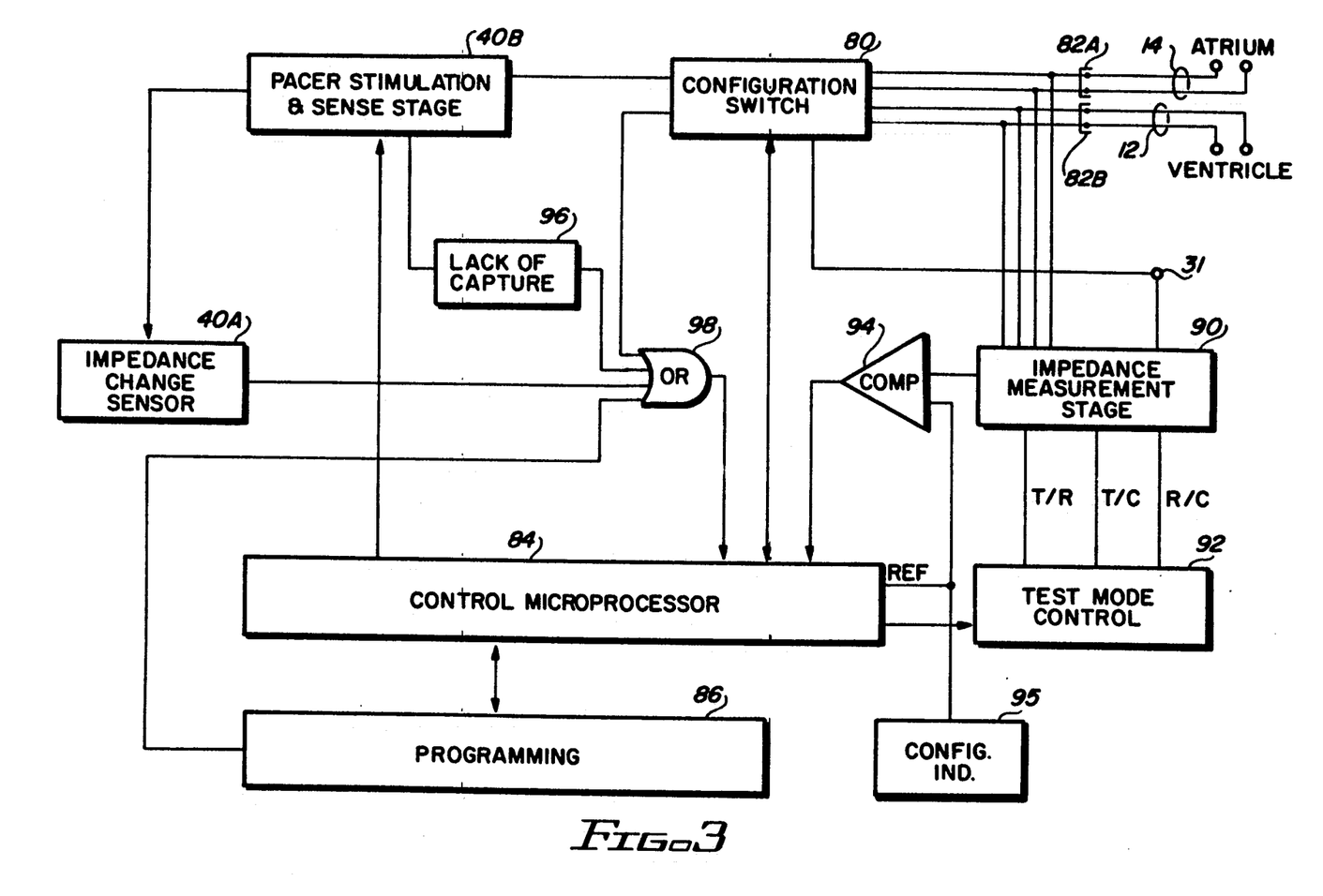
FIG. 3 is a functional block diagram showing one particular arrangement in accordance with the present invention.

FIG. 3 is a functional block diagram representing one particular arrangement in accordance with the present invention. The lead impedance analyzing circuit 40 of FIG. 2 is represented in FIG. 3 as comprising the blocks 40A and 40B. A configuration switch 80 is shown connected between pairs of leads 12 and 14 via connectors 82A, 82B and the pacing stimulation and sense stage 40B. Also shown is the connection to the case 31. In conventional fashion, a control microprocessor 84 or equivalent, is coupled to control the pacer stimulation and sense stage 40B and the configuration switch 80. A programming block 86, for programmably controlling the microprocessor 84, is telemetrically coupled to an external programming device 87.

The system of FIG. 3 is shown as further comprising an impedance measurement stage 90 coupled to be controlled by a test mode control stage 92 which in turn is controlled by the microprocessor 84. The impedance measurement stage 90 has connections to each lead in the pairs 12, 14 as well as to the pacer case 31. The output of the impedance measurement stage 90 is directed to a comparator stage 94 which receives a reference signal REF from the microprocessor 84 and is coupled to direct the results of its comparison to the microprocessor 84 for further action.

The impedance measurement stage 90 preferably measures lead impedance during the refractory period. The lead impedance analyzing circuit 40 of FIG. 2 measures impedance from the stimulation pulse and from sensed heart activity. Measurement of lead impedance as a moving average of a group of measurements (e.g., three in succession) is available at terminal 55A of the impedance measurement stage 55 of FIG. 2. If preferred, this may be substituted for the impedance measurement stage 90.

A stage 96 is coupled to the pacer stimulation and sense stage 40B to provide a signal whenever the pacemaker detects loss of capture (i.e., failure of the heart chamber to depolarize in response to an applied stimulation pulse). The ability to detect loss of capture is known in the art. See, for example, U.S. Pat. No. 4,686,988 to Sholder, entitled "Pacemaker System and Method for Measuring and Monitoring Cardiac Activity and For Determining and Maintaining Capture"; U.S. Pat. No. 4,543,956 to Herscovici, entitled "Biphasic Cardiac Pacer"; and U.S. Pat. No. 4,055,189 to Auerbach et al., entitled "Condition Monitoring Pacer", which three patents are incorporated herein by reference.

The output of the loss-of-capture stage 96 is applied to an OR gate 98, as are also signals from the configuration switch 80, impedance change sensor 40A and the programming stage 86. The OR gate 98 applies an initiation signal to the microprocessor 84 upon any one of the following events: (a) receipt of an applied signal from the configuration switch 80 corresponding to the change of connection of any of the leads at the terminals 82A, 82B; (b) a loss-of-capture signal from the stage 96; (c) a significant change of impedance signal from the sensor 40A; and (d) a signal from the programming stage 86 indicating a change in the programmed lead configuration.

An initiation signal from the OR gate 98 causes the microprocessor 84 to actuate the test mode control stage 92 to begin testing the impedance of the leads 12, 14 and the body circuit path to the case 31 in a predetermined sequence and in accordance with the particular lead configuration presently programmed. The impedance measurements performed by the stage 90 are preferably taken during a refractory period of the pacemaker. The three types of impedance measurements—T/R (tip-to-ring), T/C (tip-to-case) and R/C (ring-to-case)—are conducted in that order as described hereinabove if a bipolar configuration is programmed. If a unipolar configuration is programmed (with bipolar leads implanted), the preferred order for performing the measurements is T/C, R/C, and T/R. Once a proper impedance measurement is found, the measurement cycle is terminated and the configuration of the switch 80 is changed to correspond to operation in the available lead configuration which is detected. This new configuration is stored in the microprocessor 84 and is available as an indication from the REF lead at the configuration indicator 95.

Thus, it is seen that the present invention provides a system whereby the pacemaker seeks out, based on load recognition (the impedance load presented by the lead/tissue interface), which lead configuration is operable. If this lead configuration matches the programmed pacemaker configuration, then that is the configuration in which the pacemaker operates. However, if this lead configuration does not match the programmed pacemaker configuration (indicating either an incorrectly programmed pacemaker for the lead used or a broken conductor), then the pacemaker switches its operating configuration to the available lead configuration, thereby allowing the pacemaker to continue to pace and sense using this new lead configuration.

If a configuration change is automatically initiated by the present invention, then means are provided to signal this fact during the next interrogation of the pacemaker.

Although there have been described above specific arrangements for configuration programming of an implantable pacemaker in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. In an implantable pacemaker capable of programmably altering an electrode configuration for delivery of stimulation pulses and for sensing intracardiac signals, a system for ensuring operation of the implantable pacemaker despite incorrect programming or broken conductors, the system comprising:
   at least two pairs of electrode terminals located in the pacemaker;
   a pair of electrodes adapted for contact with body tissue, the pair of electrodes being coupled to at least one pair of electrode terminals;
   detection means for detecting an operative electrode configuration by detecting an operative combination of electrodes and electrode terminals; and
   programming means for automatically programing the pacemaker's electrode configuration to the operative electrode configuration detected by the detection means, such that the delivery of stimulation pulses and the sensing of intracardiac signals occurs in the operative electrode configuration.

2. The system of claim 1, wherein the detection means comprises:
   means for measuring an impedance between each pair of electrode terminals; and
   means for determining whether the impedance measured by the measuring means is within a preselected range.

3. The system of claim 2, wherein the detection means further comprises:
   means for detecting a loss of capture;
   means for detecting a change in the electrode configuration;
   means for detecting a significant change in the impedance between the pair of electrodes; and
   means for initiating the measuring means to measure impedance upon the occurrence of any one of a group of selected conditions of pacemaker operation, the group comprising a detected change in the electrode configuration, a detected loss of capture, and a detected significant change in the impedance measured by the measuring means.

4. In an implantable pacemaker, a system for ensuring operation of the implantable pacemaker despite incorrect programming or broken conductors, the implantable pacemaker being capable of programing an electrode configuration for delivery of stimulation pulses and for sensing intracardiac signals, the system comprising:
   a first and second pair of electrode terminals;
   a pair of electrodes adapted for contact with body tissue, the pair of electrodes being coupled to at least one pair of electrode terminals;
   measuring means for providing an impedance measurement between the first pair of electrodes terminals;
   means for determining whether the impedance measurement is within a preselected range;
   a first switching means, responsive to the determining means, for switching the measuring means to the second pair of electrode terminals when the impedance measurement of the first pair of electrode terminals is determined to be outside of the preselected range;
   means for initiating the impedance measuring means to provide an impedance measurement between the second pair of electrode terminals; and
   programming means for changing a programmed electrode configuration of the pacemaker to the pair of electrode terminals which is determined to have an impedance measurement within the preselected range.

5. The system of claim 4, wherein the first and second pair of electrodes terminals are selected from a group of pairs of electrode terminals corresponding to a tip-and-ring and a tip-and-case electrodes.

6. The system of claim 5, further comprising a third pair of electrode terminals.

7. The system of claim 6, wherein the group of pairs of electrodes further comprises ring-and-case electrode terminals, the system further comprising:
   a second switching means, responsive to the determining means, for switching the measuring means to the third pair of electrode terminals whenever the impedance measurement of the second pair of electrode terminals is determined to be outside of the preselected range; and
   means for initiating the impedance measuring means to provide an impedance measurement between the third pair of electrode terminals.

8. The system of claim 7, wherein a unipolar electrode configuration has been programmed, the first, second, and third pair of electrode terminals corresponds to the tip-and-case terminals, the tip-and-ring terminals, and the ring-and-case terminals.

9. The system of claim 7, wherein a bipolar electrode configuration has been programmed, the first, second, and third pair of electrode terminals corresponds to the tip-and-ring terminals, the tip-and-case terminals, and the ring-and-case terminals.

10. The system of claim 4, further comprising:
    means for sensing a significant change of impedance during pacemaker operation; and
    means for repeating the impedance measurement upon detection of the significant change of impedance.

11. The system of claim 4, further comprising:
    means for detecting a change in the programmed electrode configuration of the pacemaker; and
    means for repeating the impedance measurement upon a change in the programmed electrode configuration of the pacemaker.

12. The system of claim 4, further comprising:
    means for detecting a loss of capture; and
    means for repeating the impedance measurement upon detection of a loss of capture.

13. An implantable pacemaker system having the capability of programmably operating in single chamber or dual chamber modes and in a unipolar or bipolar electrode configuration, the implantable pacemaker system including an implantable pacemaker coupled to implantable pacemaker leads, the system comprising:
- a stimulation and sense stage for generating stimulating signals and for sensing heart activity;
- a configuration switch for coupling the stimulation and sense stage to the implantable pacemaker leads in accordance with a selected electrode configuration;
- a microprocessor for controlling the stimulation and sense stage and the configuration switch;
- means for programming the microprocessor to operate in a selected mode and electrode configuration of the pacemaker;
- lead impedance measurement means for measuring a lead impedance of the implantable pacemaker leads in the selected electrode configuration; and
- means for triggering the programming means to change the selected electrode configuration when the measured lead impedance of the implantable pacemaker leads is above a selected reference.

14. The system of claim 13, further comprising:
- test mode control means for initiating the lead impedance measurement means to measure lead impedance between a selected pair of electrodes.

15. The system of claim 14, wherein the test mode control means sequentially initiates the impedance measuring means to measure selectively between tip-and-ring and tip-and-case.

16. The system of claim 14, wherein the test mode control means sequentially initiates the impedance measuring means to measure selectively between tip-and-ring, tip-and-case, and ring-and-case pairs of electrodes.

17. The system of claim 14, further comprising:
- means for triggering the test mode control means to initiate a lead impedance measurement upon the occurrence of a predetermined event.

18. The system of claim 17, wherein the triggering means comprises:
- an impedance change detector, coupled to the lead impedance measurement means, for triggering the test mode control means upon the detection of a significant change of impedance.

19. The system of claim 17, wherein the triggering means comprises:
- means for detecting a change in the selected electrode configuration of the pacemaker; and
- means for triggering the test mode control means upon detecting a change in the selected electrode configuration of the pacemaker.

20. The system of claim 17, wherein the triggering means comprises:
- means for detecting a loss of capture; and
- means for triggering the test mode control means upon detection of a loss of capture.

21. The system of claim 17, wherein the triggering means comprises:
- means for triggering the test mode control means to measure lead impedance upon the occurrence of any one of a group of selected conditions of pacemaker operation, the group comprising a change in the electrode configuration initiated by the programming means, a change in the electrode configuration initiated by the test mode control means, the detection of loss of capture, and a significant change in the lead impedance measured by the lead impedance measurement means.

22. A method for ensuring operation of an implantable pacemaker system despite incorrect programming or broken electrodes, the implantable pacemaker system including an implantable lead having at least one electrode, the lead being coupled to an implantable pacemaker, the implantable pacemaker having at least two pairs of electrode terminals, the implantable pacemaker further having means for selectively programming an electrode configuration for delivery of stimulation pulses and for sensing intracardiac signals, the method comprising the steps of:
- detecting an operative electrode configuration by successively measuring an impedance between each pair of electrode terminals in a predetermined order until the impedance falls within a preselected range; and
- automatically reconfiguring the pacemaker's electrode configuration to the detected operative electrode configuration.

23. The method of claim 22, comprises the steps of:
- repeating the detecting step upon the occurrence of any one of a group of selected conditions of pacemaker operation, the group comprising a change in the electrode configuration, a loss of capture, and a significant change in the measured impedance; and
- automatically reconfiguring the pacemaker's electrode configuration to the operative electrode configuration.

24. The method of claim 22, and wherein the reconfiguring step comprises the step of:
- sequentially switching the electrode configuration to one of a unipolar (tip and a case) or a bipolar (tip and ring) configuration until an operative pair of electrodes is detected by the detection means.

25. The method of claim 22, wherein the reconfiguring step comprises the step of:
- sequentially switching the electrode configuration to one of a unipolar (tip and case), a bipolar (tip and ring), or a unipolar (ring and case) configuration until an operative pair of electrodes is detected by the detection means.

26. A system for ensuring operation of the implantable pacemaker despite incorrect programming or broken conductors, the system comprising:
- an implantable lead having a selected one of a tip electrode or a tip and a ring electrode, the tip electrode or the ring electrode being adapted for contact with body tissue, each electrode having a conductor with an impedance associated therewith;
- a pulse generator, coupled to the implantable lead, for generating stimulation pulses;
- sensing means, coupled to the implantable lead, for sensing intracardiac signals;
- a pacemaker case for housing the pulse generator and the sensing means, the pacemaker case acting as a case electrode;
- means for programming an electrode configuration for the pulse generator means and for the sensing means;
- switching means, responsive to the programming means, for switchably connecting a pair of electrodes to the pulse generator and the sensing means;
- means for detecting an operative electrode configuration by detecting a stimulation impedance within a prescribed range, the stimulation impedance being the combined impedance of the pair of electrodes with the corresponding conductors and the body tissue impedance which results from a stimulation pulse delivered to body tissue; and means for automatically reprogramming the pacemaker's electrode configuration to the operative electrode configuration detected by the detection means.

27. The system of claim 26, wherein the pair of electrodes are selected from the group comprising a tip and ring electrode, a tip and case electrode, and a ring and case electrode.

28. A system for ensuring operation of the implantable pacemaker despite incorrect programming or broken conductors, the system comprising:

an implantable lead having a selected one of a tip electrode or a tip and a ring electrode, the tip electrode or the ring electrode being adapted for contact with body tissue, each electrode having a conductor with an impedance associated therewith;

a pulse generator, coupled to the implantable lead, for generating stimulation pulses;

sensing means, coupled to the implantable lead, for sensing intracardiac signals;

a pacemaker case for housing the pulse generator and the sensing means, the pacemaker case acting as a case electrode;

means for programming an electrode configuration for the pulse generator means and for the sensing means;

switching means, responsive to the programming means, for switchably connecting a pair of electrodes to the pulse generator and the sensing means, the selected from the group of pairs of electrodes comprising a tip and ring electrode, a tip and case electrode, and a ring and case electrode;

means for detecting an operative electrode configuration by detecting an impedance within a prescribed range; and means for automatically reprogramming the pacemaker's electrode configuration to the operative electrode configuration detected by the detection means.

29. The system of claim 28, wherein the prescribed range is 200–1500 ohms.

* * * * *